(12) United States Patent
Kang et al.

(10) Patent No.: US 10,582,841 B2
(45) Date of Patent: Mar. 10, 2020

(54) DARK FIELD ENDOSCOPIC MICROSCOPE

(75) Inventors: Jin U. Kang, Ellicott City, MD (US); Xuan Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 553 days.

(21) Appl. No.: 13/464,643

(22) Filed: May 4, 2012

(65) Prior Publication Data

US 2012/0283516 A1 Nov. 8, 2012

Related U.S. Application Data

(60) Provisional application No. 61/482,299, filed on May 4, 2011.

(51) Int. Cl.
*A61B 1/00* (2006.01)
*A61B 1/06* (2006.01)
*A61B 1/07* (2006.01)

(52) U.S. Cl.
CPC ........ *A61B 1/0623* (2013.01); *A61B 1/00165* (2013.01); *A61B 1/0684* (2013.01); *A61B 1/07* (2013.01); *A61B 1/00188* (2013.01)

(58) Field of Classification Search
CPC ... A61B 1/07; A61B 1/00096; A61B 1/00062; A61B 1/00165–0017; A61B 1/04–055
USPC ................ 600/109, 129, 136, 160, 168, 182
See application file for complete search history.

(56) References Cited

U.S. PATENT DOCUMENTS

| | | | | |
|---|---|---|---|---|
| 4,579,419 A | * | 4/1986 | Scrivo | G02B 6/3855 362/573 |
| 5,434,669 A | * | 7/1995 | Tabata | A61B 1/042 356/241.5 |
| 5,673,144 A | * | 9/1997 | Chastang et al. | 359/385 |
| 6,370,422 B1 | * | 4/2002 | Richards-Kortum et al. | 600/478 |
| 6,498,948 B1 | * | 12/2002 | Ozawa | A61B 1/00183 348/E7.087 |
| 6,527,708 B1 | * | 3/2003 | Nakamura | A61B 1/00096 600/109 |
| 8,452,384 B2 | * | 5/2013 | Ince | A61B 5/0261 600/343 |
| 8,848,185 B2 | * | 9/2014 | Barak | G01B 11/02 356/369 |
| 9,131,861 B2 | * | 9/2015 | Ince | A61B 1/042 |
| 9,216,015 B2 | * | 12/2015 | Wilson | A61B 17/3431 |
| 9,292,918 B2 | * | 3/2016 | Zagrodsky | G06T 7/0012 |
| 9,297,749 B2 | * | 3/2016 | Micheels | G01N 21/359 |

(Continued)

OTHER PUBLICATIONS

Chen et al., "Experimental and theoretical analysis of core-to-core coupling on fiber bundle imaging," Opt. Express 16, 21598-21607 (2008).

Flusberg et al., "Fiber-optic fluorescence imaging," Nat. Methods. 2, 941-950. (2005).

(Continued)

*Primary Examiner* — Timothy J Neal
*Assistant Examiner* — William B Chou
(74) *Attorney, Agent, or Firm* — Venable LLP; Henry J. Daley; Laura G. Remus

(57) ABSTRACT

A dark field endoscopic microscope includes an illumination system, an objective lens unit arranged in an optical path of the illumination system, an optical fiber bundle optically coupled to the objective lens unit, and an observation system arranged in an optical return path from the optical fiber bundle. The illumination system provides oblique off-axial illumination while axial rays are at least attenuated.

12 Claims, 7 Drawing Sheets

(56) References Cited

U.S. PATENT DOCUMENTS

| | | | | |
|---|---|---|---|---|
| 9,324,141 | B2* | 4/2016 | Begin | G06T 5/002 |
| 9,383,263 | B2* | 7/2016 | Welford | A61B 5/0066 |
| 2003/0076571 | A1* | 4/2003 | MacAulay | G02B 21/0028 |
| | | | | 359/237 |
| 2007/0232874 | A1* | 10/2007 | Ince | A61B 5/0261 |
| | | | | 600/320 |
| 2010/0030020 | A1* | 2/2010 | Sanders et al. | 600/109 |
| 2011/0137126 | A1* | 6/2011 | French | A61B 1/00165 |
| | | | | 600/178 |

OTHER PUBLICATIONS

Gmitro et al., "Confocal microscopy through a fiber-optic imaging bundle" Opt. Lett. 18, 565-567 (1993).

Göbel et al., "Miniaturized two-photon microscope based on a flexible coherent fiber bundle and a gradient-index lens objective," *Opt. Lett.* 29, 2521-2523 (2004).

Han et al., "Pixelation effect removal from fiber bundle probe based optical coherence tomography imaging," *Opt. Express.* 18, 7427-7439 (2010).

Han et al., "Common path optical coherence tomography with fibre bundle probe," *Electron. Lett.* 45(22), 1110-1112 (2009).

Juškaitis et al., "Real-time white light reflection confocal microscopy using a fibreoptic bundle" Scanning 19, 15-19 (1997).

Lane, "Reflection-contrast limit of fiber-optic image guides," J Biomed. Opt., vol. 14, 064028 (2009).

Lane, "Terminal reflections in fiber-optic image guides," Appl. Opt. 48(30), 5802-5810 (2009).

Liang et al., "Fiber confocal reflectance microscope (FCRM) for in-vivo imaging," *Opt. Express.* 9, 821-830 (2001).

Muldoon et al., "Subcellular-resolution molecular imaging within living tissue by fiber microendoscopy," Opt. Express 15, 16413-16423 (2007).

Sun et al., "Needle-compatible single fiber bundle image guide reflectance endoscope", *J. Biomed. Opt.*, 15, 040502 (2010).

Villiger et al., "Dark-field optical coherence microscopy," *Opt. Lett.* 35, 3489-3491 (2010).

Xie et al., "Fiber-optic-bundle-based optical coherence tomography," *Opt. Lett.* 30, 1803-1805 (2005).

\* cited by examiner

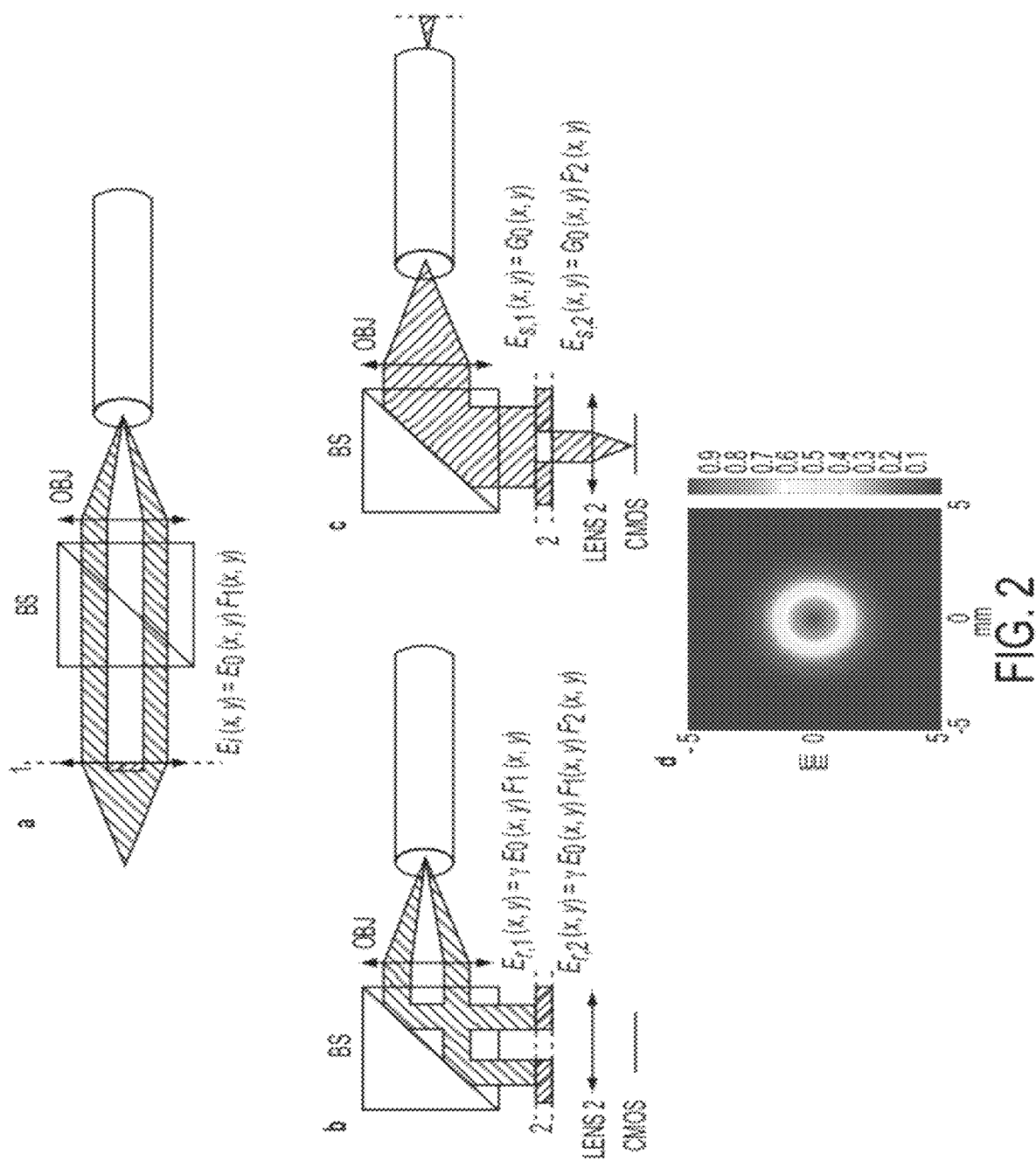

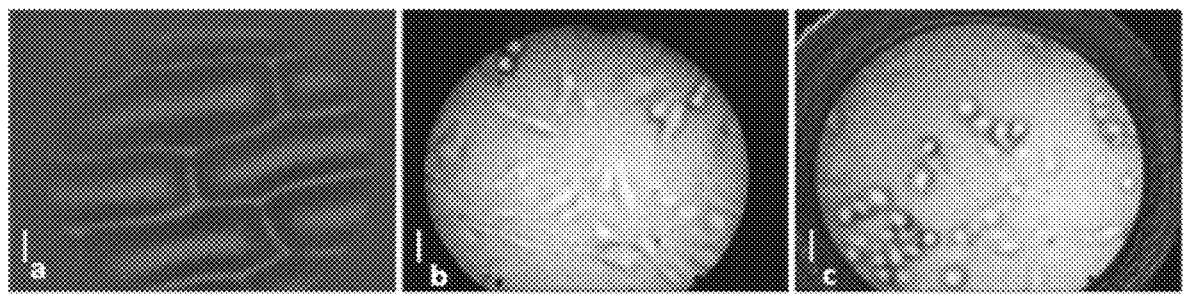
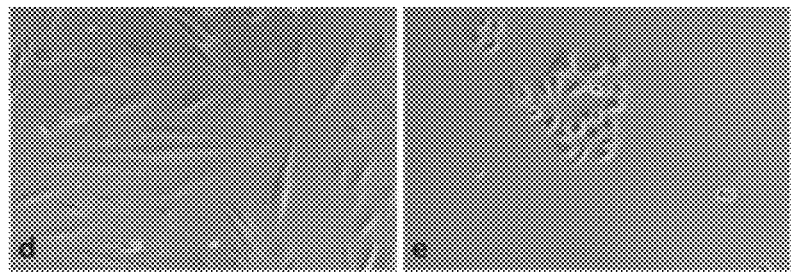
FIGS. 7A-7E

DARK FIELD ENDOSCOPIC MICROSCOPE

CROSS-REFERENCE OF RELATED APPLICATION

This application claims priority to U.S. Provisional Application No. 61/482,299 filed May 4, 2011, the entire contents of which are hereby incorporated by reference.

This invention was made with Government support under Grant Nos. 1R01 EB 007969-01 and R21 1R21NS063131-01A1, awarded by the National Institutes of Health (NIH). The U.S. Government has certain rights in the invention.

BACKGROUND

1. Field of Invention

The field of the currently claimed embodiments of this invention relates to dark field endoscopic microscopes.

2. Discussion of Related Art

Various endoscopic microscopy techniques have been developed for in situ pathology and visual examinations. Flexible optical fiber bundles have been widely used in such endoscopic microscopy applications [1-9]. The use of a fiber bundle allows visual access to the specimen deep within the body cavity. The fiber bundle imaging also offers a very simple imaging probe configuration, which is why it is widely favored by many endoscopic applications. By using an imaging fiber bundle for light delivery, a scanning mechanism in front of the specimen can be eliminated, and images can be formed by scanning a focused light spot at the proximal end of the fiber bundle, pixel by pixel, as in fiber bundle based laser scanning fluorescence imaging [1], fiber confocal reflectance microscopy [2], two-photon imaging [3], and optical coherence tomography [4-6]. Such a system can achieve high spatial resolution and large dynamic range. A simpler endoscopic configuration is a scan-less fiber bundle endoscopic imager interfaced with a 2D camera for direct imaging of tissue [7, 10]. It is an attractive design to use only one fiber bundle for illumination and image acquisition in a reflectance fiber-bundle microscope (RFM), since such design can help to further miniature the endoscopic probe and reduce the system cost. However, the dual illumination and image acquisition configuration has an inherent drawback: the specular reflectance from the end facets of the fiber bundle can be orders of magnitude larger than the backscattered light from the sample [11, 12]. The specular reflection takes up a significant portion of the limited dynamic range of the detector and thus decreases the image contrast. The resultant large background level also increases the overall noise level, which hinders the efficient detection of the signals of interest. Recently, J. Sun et al used a cross polarization detection technique in the reflectance fiber bundle endoscope set-up to suppress the specular reflection from the proximal end of the fiber bundle [10]. Therefore, there remains a need for improved endoscopic microscopes.

SUMMARY

A dark field endoscopic microscope according to an embodiment of the current invention includes an illumination system, an objective lens unit arranged in an optical path of the illumination system, an optical fiber bundle optically coupled to the objective lens unit, and an observation system arranged in an optical return path from the optical fiber bundle. The illumination system provides oblique off-axial illumination while axial rays are at least attenuated.

BRIEF DESCRIPTION OF THE DRAWINGS

Further objectives and advantages will become apparent from a consideration of the description, drawings, and examples.

FIG. 2 illustrates a ray tracing analysis of the dark field endoscopic microscope of FIG. 1, in which: (a) Optical path of illumination light; (b) optical path of light that is specularly reflected from the fiber bundle end; (c) optical path of signal light back-scattered by the specimen and guided by the fiber bundle; (d) simulated distribution of optical field exiting from a single fiber core at plane 2.

FIGS. 7A-7E show (a) Onion skin cells; (b) KAT-18 cells; (c) FTC-133 cells; (d) both cells: KAT-18 and FTC-133. Scale bars represent 50 µm; Phase contrast microscopic image of KAT-18 cells (d) and FTC-133 cells (e).

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention provide a dark-field illuminated reflectance mode endoscopic microscope based on a miniature fiber bundle probe for both illumination and signal collection. The dark-field illumination technique according to some embodiments of the current invention can suppress specular reflection similar to techniques such as cross polarization detection and differential interference contrast [13]. Although it has been widely used in conventional microscopes, dark-field illumination has only recently been incorporated into other imaging systems. For example, it was used in optical coherence microscopy to reduce specular reflection from cover slides for cell imaging [14].

Experimental results demonstrate that dark-field illumination according to some embodiments of the current invention can effectively suppress the specular reflection from the proximal end of the fiber bundle and provide high contrast imaging. We built a dark-field illuminated reflectance fiber-bundle endoscopic microscope (DRFM) according to an embodiment of the current invention that achieved a 4.4 μm lateral resolution. To show that the DRFM can provide high resolution, high contrast images, we used it to study the morphologies of cells, including onion skin cells and two types of thyroid cancer cells. Still and video images are presented in some examples.

Figure 1:
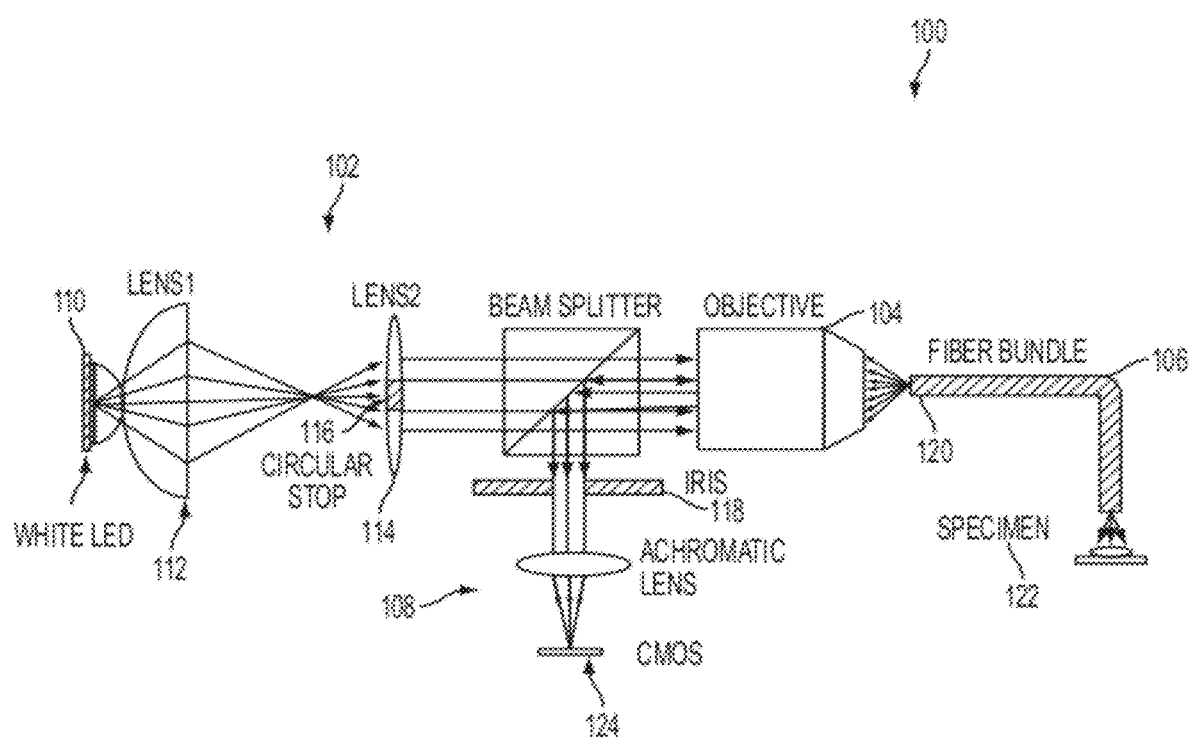
FIG. 1 is a schematic illustration of a dark field endoscopic microscope according to an embodiment of the current invention.

FIG. 1 is a schematic illustration of a dark field endoscopic microscope 100 according to an embodiment of the current invention. The dark field endoscopic microscope 100 includes an illumination system 102, an objective lens unit 104 arranged in an optical path of the illumination system 102, an optical fiber bundle 106 optically coupled to the objective lens unit 104, and an observation system 108 arranged in an optical return path from the optical fiber bundle 106. The illumination system 102 provides oblique off-axial illumination while axial rays are at least attenuated.

In some embodiments, the illumination system 102 can include a light source 110, a collimating lens system (112, 114), and an opaque disk 116 arranged to block axial rays from the light source 110. In some embodiments, the light source 110 can be a white light source, such as, but not limiting to, a white light emitting diode (LED). In other embodiments, the light source 110 can be a narrowband light source, such as, but not limited to, a narrowband LED.

In some embodiments, the observation system 108 can include an aperture stop 118 arranged to block specular reflection of illumination light from a proximal end 120 of the optical fiber bundle 106 while allowing light returned from a specimen 122 under observation to pass therethrough. In some embodiments, the aperture stop 118 can be, but is not limited to, an adjustable iris.

In some embodiments, the observation system 108 can include an imaging detector 124 arranged after the aperture stop 118 to provide imaging signals for digital imaging.

In some embodiments, the optical fiber bundle 106 can be replaceable such that a used optical fiber bundle can be replaced by a sterile optical fiber bundle for surgical use. For example, the optical fiber bundle can be, but is not required to be, disposable such that a new, sterile optical fiber bundle can be used for each procedure.

Examples

The following examples are provided to help explain some concepts of the current invention. The broad concepts of the current invention are not limited to these specific examples.

FIG. 1 shows the schematic illustration of the DRFM system for use in the following examples. We used a white LED (Thorlabs, MCWHL2, viewing angle 140°) followed by a set of lenses for illumination. The distances between LED, lens1 and lens2 (LB1811, f=35 mm, Ø1") are adjusted, so that the optical field effectively covers the aperture of lens2 and light is almost collimated after lens2. A polarization-insensitive beam-splitter (CM1-BS013, Thorlabs) is used to direct the illumination light into the imaging bundle and direct the return image to a camera. The probe arm consists of a microscopic objective (Nikon, 10×, NA=0.25) and a fiber bundle (Fujikura, FIGH 500N) with an image circle diameter of 460 μm. The average core size of the fiber bundle is 2.9 μm and the average pitch is 4.5 μm. The incident end of the fiber bundle is on the focal plane of the objective. The flexible fiber bundle delivers light to the imaging site, collects backscattered photons, and delivers them to the camera set-up. Since no focusing objective was used at the distal end of the fiber bundle, the images were obtained while the samples were within the beam diffraction length of the fiber bundle mode. Images were sharp when the fiber bundle tip was within the diffraction length to the sample surface; image blurred when the tip was far away from the sample surface, due to the beam diverging. In the camera set-up, a doublet achromatic lens (Thorlabs, AC254-150-A-ML) focuses the light on the 2D CMOS imaging sensor interfaced with USB2.0 (DCC1645C, 1280×1024, Thorlabs). All images in this section are in 8-bit gray scale. In the recorded images, each pixel represents 0.44 μm image width, and scale bars represent 50 μm. To increase the image contrast and remove the pixilation effect due to individual fiber cores of the fiber bundle, we applied histogram equalization together with the Gaussian filtering to the original images (shown in FIG. 6B, FIG. 7A-7C) [6].

The dark-field illumination is achieved by differentiating illumination and detection light paths. In the illumination path, we block the central light rays along the optical axis using an opaque disk with a diameter of 6 mm, so that only the oblique rays illuminate the proximal end of the fiber bundle. As a result of the annular illumination, the rays reflected from the proximal end of fiber bundle are also oblique and would carry only high spatial frequency information of the image plane. We use an iris in the detection arm to serve as a low-pass filter and to reject specular rays due to their high spatial frequency. On the other hand, light reflected or scattered by the sample is collected at the distal end of the fiber bundle and guided by the cores of the fiber bundle. Therefore, most of the energy of the signal light is concentrated at the central part of the beam which corresponds to low spatial frequency. Although the iris may also filter out signal light slightly, a significant portion of the signal light is detected by the camera.

The principle of DRFM is illustrated more explicitly in FIG. 2 and analyzed based on geometric optics. The illumination light path is shown in FIG. 2(a); the specular reflection and signal light paths are shown in FIGS. 2(b) and (c), respectively.

As one can see from FIG. 2(a), due to the existence of the circular optical stop, the optical field at plane 1 can be expressed as:

$$E_i(x,y) = E_0(x,y) F_1(x,y) \quad (1)$$

In Equation (1), x and y are spatial coordinates; $E_0(x,y)$ is the optical field distribution before the optical stop; $F_1(x,y)$ describes the transmission of the circular stop with radius $r_1$:

$$F_1(x, y) = \begin{cases} 0 & (\sqrt{x^2 + y^2} \leq r_1) \\ 1 & (\sqrt{x^2 + y^2} > r_1) \end{cases} \quad (2)$$

FIG. 2(b) shows the path of light that is specularly reflected from the fiber bundle end. Simply using the law of reflection, we can express the optical field incident to plane 2 as $\gamma E_i(x,y)$, in which γ is a coefficient taking into account the reflectivity of the fiber bundle end and the system's efficiency. Therefore, after the iris, the optical field becomes $E_{r,2}(x,y)=\gamma E_0(x,y)F_1(x,y)F_2(x,y)$ in which $F_2(x,y)$ is the transmission function of the iris:

$$F_2(x,y) = \begin{cases} 0 & (\sqrt{x^2+y^2} > r_2) \\ 1 & (\sqrt{x^2+y^2} \le r_2) \end{cases} \quad (3)$$

Adjusting the aperture size of the iris so that $r_2 \le r_1$, we can ensure that $F_1(x,y)F_2(x,y)$ always equals 0 and therefore reject all the specular light from hitting the CMOS camera. In the setup, $r_1$ (3 mm) was chosen experimentally which provided the optimized images.

Signal photons backscattered by the sample follow a different path, as shown in FIG. 2(c). This is because the geometry of light beam exiting the fiber bundle is determined by the modes supported by the fiber. Unlike traveling in free space, light incident into the fiber bundle will be coupled into the guided modes determined by the physical properties of the fiber bundle. Therefore, photons traveling in guided mode in a fiber core will "forget" the illumination configuration. As shown in FIG. 2(c), the light backscattered by the specimen will couple into individual cores of the fiber bundle and travel in guided mode until arriving at the proximal end of the fiber bundle. The output beam will form a cone with a diverging angle determined by the numerical aperture (NA) of the fiber bundle. Therefore, $G_0(x,y)$, the optical field at plane 2 corresponding to the signal photons, is prominently different from $E_i(x,y)$, and is usually maximized at the beam center. We can consider the optical field exiting from an individual core as a Gaussian beam. The waist of the Gaussian beam, the end facet of the fiber bundle, and the front focal plane of the objective coincide in this set-up. Let's assume that the waist of the Gaussian beam equals the radius of the cores in the fiber bundle which is 1.45 μm; the focal length of objective is 15 mm; plane 2 is about 20 cm away from the objective. With these parameters, we can estimate the beam radius $w_2$ at plane 2 using ABCD matrix. Based on the value of $w_2$, we can obtain the optical field at plane 2, which is $g_2(x,y)=g_0 e^{+(x^2+y^2)w_2^2}$ [15]. The result is shown in FIG. 2(d). $G_0(x,y)$, which in fact is the superimposition of the fields from the different cores, should resemble $g_2$, due to the small diameter of the fiber bundle and spatial incoherence of the LED. As seen from FIG. 2(d), the energy of optical field is concentrated at the center of beam. As a result, although the iris causes some signal loss, the optical field that passes the iris, $E_{r,2}(x,y)=G_0(x,y)F_2(x,y)$, still contains a relatively unattenuated light signal from the specimen and is imaged by the CMOS camera.

Figure 3A:
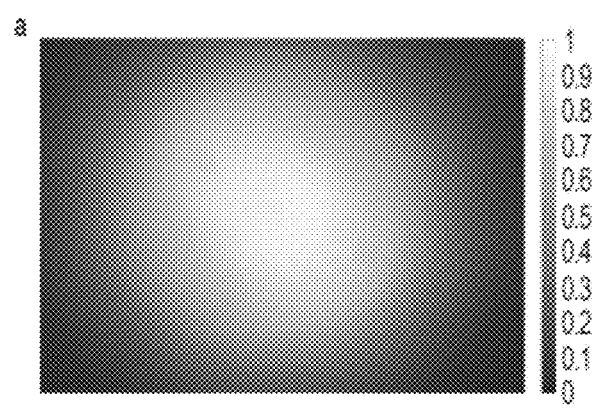
FIG. 3A shows transverse profile of a beam exiting from the fiber bundle according to an embodiment of the current invention.
Figure 3B:
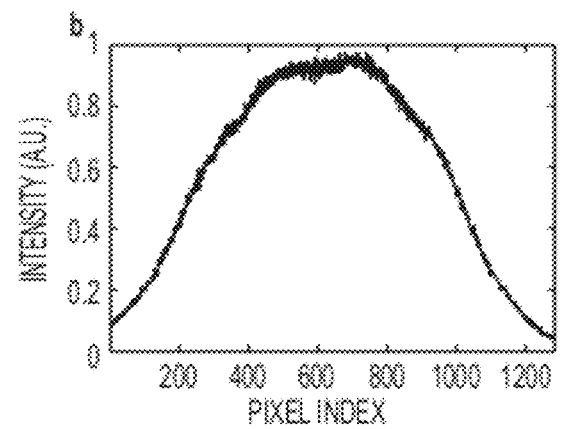
FIG. 3B shows signal intensity along the $512^{th}$ row of the FIG. 3A.

Results:

To verify that the energy output from the fiber bundle is concentrated in central rays even when an annular illumination shown in FIG. 2(a) is used, we recorded the distribution of the optical field exiting from the fiber bundle by directly placing the camera in front of the distal end of the fiber bundle without a lens. We adjusted the distance between the camera's sensor array and the fiber bundle end so that the detector could cover the whole optical field exiting the fiber bundle. The optical field obtained is shown in FIG. 3A, which has its intensity maximized at the beam center. Signal intensity along the $512^{th}$ row of the FIG. 3A is shown in FIG. 3B, which is bell shaped.

Figure 4A:
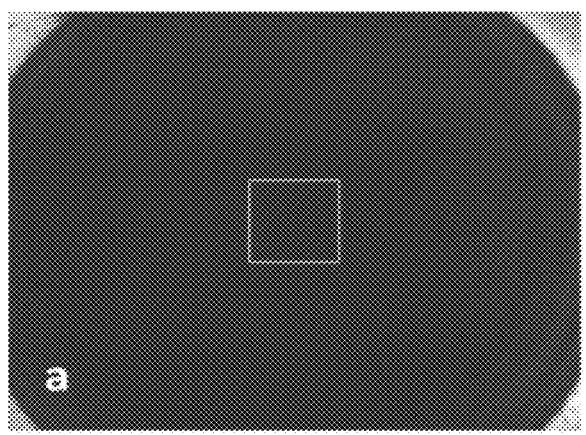
FIGS. 4A and 4B show reflectance images of the fiber bundle tip obtained at the same experimental conditions (a) with the dark-field illumination, (b) without the dark-field illumination.
Figure 4B:
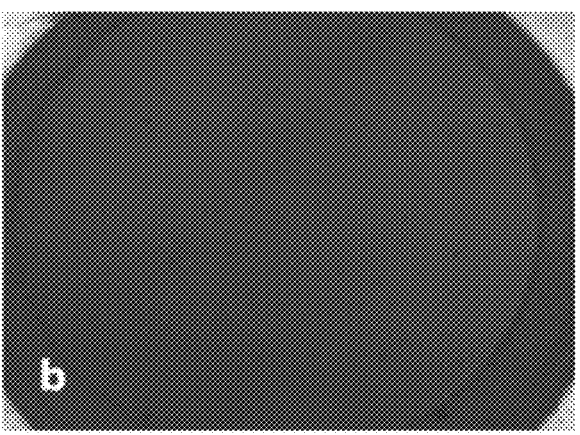

To show that dark-field illumination can effectively suppress the specular reflection at the entrance end of the fiber bundle, we compared images obtained from DRFM and RFM (without dark-field illumination). Without a specimen, we obtained FIG. 4A when the opaque disk was used to block the central rays and the iris aperture was adjusted accordingly. Keeping the same LED power level, the same aperture size of the iris, and the same exposure time of the CMOS camera as when FIG. 4A was taken, we obtained FIG. 4B by simply removing the opaque disk from the optical path. Comparing FIGS. 4A and 4B, we can clearly see that dark-field illumination effectively suppressed the end reflection. We also took images with only optical stop at plane 1 or only aperture at plane 2, under the same imaging condition (camera integration time and LED output power were kept the same). We averaged the signal intensity within the square shown in FIG. 4A for each image, and normalized the resultant intensities using the one obtained without the iris or the stop. The results are summarized in Table 1, which quantitatively shows dark-field illumination can effectively suppress the specular reflection.

TABLE 1

Averaged signal intensity at the central part of fiber bundle when both iris and stop are inserted into the optical path; when either iris or stop is inserted; and when neither of them are inserted.

| With both iris and stop | With iris | With stop | With neither iris nor stop |
|---|---|---|---|
| 0.08 | 0.31 | 0.65 | 1 |

Figures 5A, 5B, 5C, 5D:
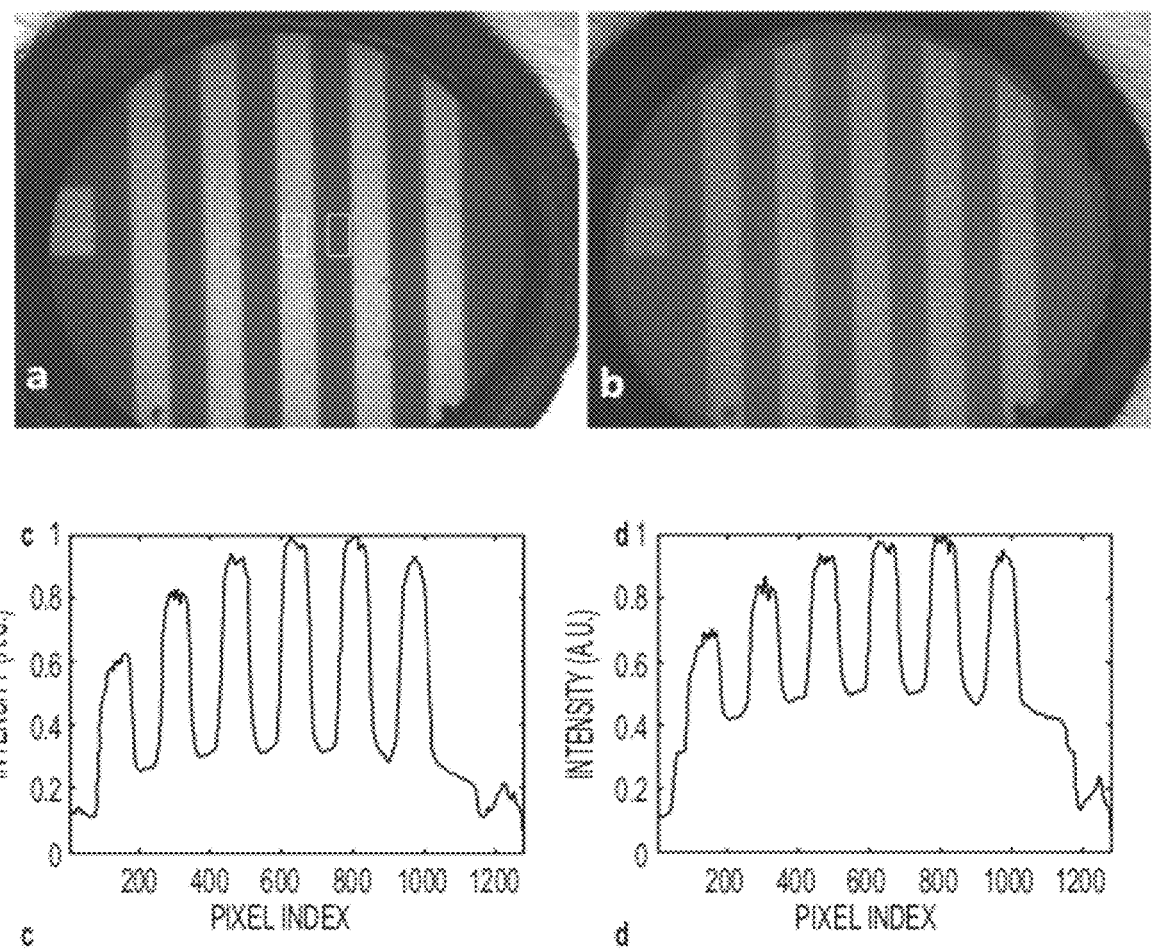
FIGS. 5A-5D show reflectance images of NBS 1963A resolution target (a) with Dark-field illumination; (b) without dark-field illumination; (c) image intensity along the $512^{th}$ row of the image after Gaussian filtering FIG. 5A; (d) image intensity along the $512^{th}$ row of image after Gaussian filtering FIG. 5B.

To further demonstrate that the reduced specular reflection can improve the image contrast, we imaged NBS 1963A resolution target (Edmund Optics) and show the images of bars (14 cycles/mm) obtained using DRFM and RFM in FIG. 5A and FIG. 5B. An optical stop was inserted and the aperture of iris was adjusted to achieve dark-field illumination. We maintained the same experimental setting when obtaining FIGS. 5A and 5B, such as the diameter of the iris, the LED power level, the exposure time of the CMOS camera, as well as the distance between the end of imaging fiber bundle and the surface of the resolution target. Moreover, the image bundle was nearly touching the resolution target in taking FIGS. 5A and 5B; hence there was no remarkable defocusing in both images. To compare the contrast, we normalized both images to their maximum signal intensities within the image circle. Due to the normalization, bars in FIG. 5A look brighter than in FIG. 5B as the dark-field illumination increased the image contrast. Clearly, bars in FIG. 5A exhibit much higher visibility than in FIG. 5B. To remove the signal fluctuation due to the fiber bundle's pixilation, we applied a Gaussian filter with a standard deviation of 4 pixels to FIGS. 5A and 5B and the resultant image intensity along the central ($512^{th}$) row of the filtered images is shown in FIG. 5C and FIG. 5D (normalized to their maximum values). FIG. 5C clearly shows higher contrast between the high reflectivity and low reflectivity part of the resolution target. To show the contrast enhancement quantitatively, we calculated the mean signal intensity enclosed in the left rectangle shown in FIG. 5A and denoted the result as $I_{target}$. We also calculated the mean signal intensity enclosed in the right rectangle and denoted the result as $I_{background}$. Using $I_{target}$ and $I_{background}$, we could calculate the local contrast $C_{dark}=(I_{target}-I_{background})/I_{background}$ of the image shown in FIG. 5A that was obtained using darkfield illumination. Similarly, we could also calculate $C_{bright}$ using the averaged signal intensity within the same areas. The resultant $C_{dark}$ is 1.88 and $C_{bright}$ is 0.88, which indicates we have achieved a more than two-fold improvement on the local contrast by using dark-field illumination.

Figure 6A:
FIG. 6A shows unprocessed image of US 1951 Air Force target obtained from DRFM.
Figure 6B:
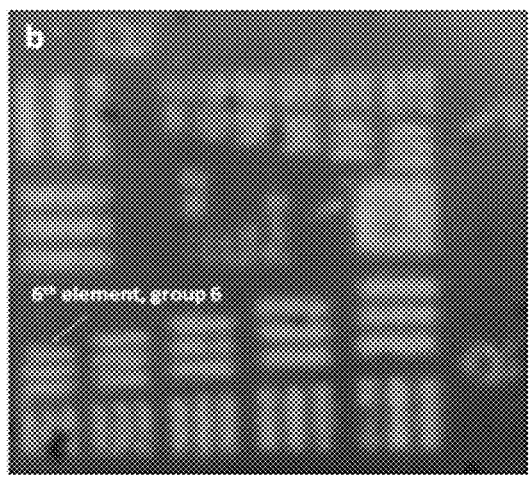
FIG. 6B shows the image obtained by enhancing FIG. 6A using histogram equalization and Gaussian filtering.

We tested the spatial resolution of DRFM by imaging a U.S. 1951 Air Force target and show the result in FIG. 6A. We enhanced image contrast and removed pixilation effects using an algorithm developed by J. Han et al. The result is shown as FIG. 6B in which the $6^{th}$ element in group 6 is clearly discernable as indicated by the arrow. This implies our DRFM has a resolution in the order of 4.4 μm (114 line pairs/mm), which is limited by the size of the fiber bundle cores.

To evaluate DRFM according to an embodiment of the current invention, we imaged different types of cells. FIG. 7A shows a DRFM image of onion skin cells. The hexagon cell walls are clearly resolved. Video 1 shows images of onion cells when the probe is approaching the sample. Since no imaging optics is used at the distal end of the fiber bundle, when the probe is far away from the sample, the image is blurred due to the diverging of the light beam or so called "de-focusing" effect. The cells' structures become sharper in the images when the probe is in close proximity of the sample.

We also obtained intrinsic contrast images from label-free cell samples to demonstrate the high sensitivity of our system. It is challenging to image cultured label-free cells using a reflectance mode microscope due to the low refractive index mismatch between cells and the liquid where cells reside. Therefore, such cell samples are good test subjects for our DRFM. We imaged two thyroid cancer cell lines—KAT-18 and FTC-133—which were seeded in a 24-well plate and imaged after 2 days of culturing. To mimic the endoscopic imaging situation, we took images of the cancer cells by hand-holding the fiber bundle probe and dipping the probe into the nutrient solution. FIGS. 7B and 7C (also Videos 2 and 3) were obtained by imaging a sample containing KAT-18 cells and a sample containing FTC-133 cells. KAT-18 cells are known to have a more elongated shape than FTC-133 cells. As a reference, we took images of KAT-18 and FTC-133 cells using a conventional phase contrast microscope (Nikon Eclipse Ti, magnification: 100) and show the results in FIGS. 7D and 7E, which exhibit the same cell morphologies as in FIGS. 7B and 7C.

Discussion

In this section, we only considered the suppression of the specular reflection originating from the proximal end of the fiber bundle. Although the distal end of the fiber bundle also results in specular reflection, the reflected light from the distal end usually exhibits significantly less intensity than that from the proximal end. One reason is that the distal end is usually immersed in a water-like medium which has a refractive index more similar to the fiber bundle, while the proximal end of fiber bundle is in the air which has a refractive index significantly different from fiber bundle's refractive index and leads to a much stronger Fresnel reflection. Another reason is that the coupling loss of the incoherent light source (white LED) to fiber bundle and the fiber loss results only a fraction of the source photons can arrive at the distal end of fiber bundle.

We used an opaque disk to stop the central rays of the illumination light to achieve dark-field illumination. We chose the diameter of the optical stop based on the systematic experiment that shows the best image contrast. However an optimal disk size varies if any component of the imaging system is changed. The overall system efficiency depends not only on the size of the optical stop, but also depends on the NA of the microscope objective and the NA of the fiber bundle. Theoretically, when the NA of the objective equals the NA of the fiber bundle, which is 0.39, the coupling efficiency is optimized [16]. However, when we used an objective with a larger magnification and thus higher NA (NA=0.4), the uniformity of the LED illumination was significantly degraded. As a result, we chose to use an objective with $NA_{obj}$=0.25. Moreover, to effectively illuminate the sample, we needed to make sure that the size of the circular stop at plane 1, or size of the iris at plane 2 is smaller than the aperture of the objective. Therefore, the numerical aperture of acceptance cone, $NA_{accept}$, has to be smaller than $NA_{ON}$, which is 0.25. If $NA_{accept}$ is too small compared to $NA_{obj}$, most of the signal power will be rejected due to the small diameter of the aperture at plane 2; if $NA_{accept}$ is close to $NA_{obj}$, the intensity if illumination light is small due to the large optical stop. As a result, there exists an optimized $NA_{accept}$ between 0 and 0.25 and we empirically chose the diameter of the stop to be 6 mm and thus $NA_{accept} \approx 0.2$ for optimizing the image contrast. However, as discussed above, the system efficiency does not have a straightforward functional dependency on the NAs. Therefore, numerical simulation is necessary to determine the parameters that optimize the imaging system.

CONCLUSION

In this section, we experimentally demonstrated a high-resolution DRFM according to an embodiment of the current invention which is capable of providing high-resolution endoscopic imaging. This DRFM system is cost effective, compact, and uses one fiber bundle for both illumination and imaging. We used a dark-field illumination configuration to suppress specular reflection at the proximal end of the fiber bundle. The DRFM used in the experiment achieved a 4.4 μm spatial resolution, which is limited by the pitch and diameter of element fiber cores in the imaging bundle. Video imaging was performed to validate its use for cell morphology.

REFERENCES

[1] B. A. Flusberg, E. D. Cocker, W. Piyawattanametha, J. C. Jung, E. L. Cheung, and M. J. Schnitzer, "Fiber-optic fluorescence imaging," *Nat. Methods.* 2, 941-950. (2005).

[2] C. Liang, M. Descour, K. B. Sun, and R. Richards-Kortum, "Fiber confocal reflectance microscopy (FCRM) for in-vivo imaging," *Opt. Express.* 9, 821-830 (2001).

[3] W. Göbel, J. N. D. Kerr, A. Nimmerjahn, and F. Helmchen, "Miniaturized two-photon microscope based on a flexible coherent fiber bundle and a gradient-index lens objective," *Opt. Lett.* 29, 2521-2523 (2004)

[4] T. Xie, D. Mukai, S. Guo, M. Brenner, and Z. Chen, "Fiber-optic-bundle-based optical coherence tomography," *Opt. Lett.* 30, 1803-1805 (2005)

[5] J. Han, X. Liu, C. G. Song, and J. U. Kang, "Common path optical coherence tomography with fibre bundle probe," *Electron. Lett.* 45(22), 1110-1112 (2009).

[6] J. Han, J. Lee, and J. U. Kang, "Pixelation effect removal from fiber bundle probe based optical coherence tomography imaging," *Opt. Express.* 18, 7427-7439 (2010)

[7] T. J. Muldoon, M. C. Pierce, D. L. Nida, M. D. Williams, A. Gillenwater, and R. Richards-Kortum, "Subcellular-resolution molecular imaging within living tissue by fiber microendoscopy," *Opt. Express* 15, 16413-16423 (2007)

[8] A. F. Gmitro, D. J. Aziz, "Confocal microscopy through a fiber-optic imaging bundle" *Opt. Lett.* 18, 565-567 (1993).

[9] R. Juškaitis, T. Wilson, T. F. Watson, "Real-time white light reflection confocal microscopy using a fibreoptic bundle" *Scanning* 19, 15-19 (1997).

[10] J. Sun, C. Shu, B. Appiah, and R. Drezek, "Needle-compatible single fiber bundle image guide reflectance endoscope", *J. Biomed. Opt.*, 15, 040502 (2010).

[11] P. Lane, "Terminal reflections in fiber-optic image guides," Appl. Opt. 48(30), 5802-5810 (2009).

[12] P. Lane, "Reflection-contrast limit of fiber-optic image guides," *J. Biomed. Opt., Vol.* 14, 064028 (2009)

[13] R. O. Wayne, Chap. 6-9, "Light and video microscopy," Boston: Academic Press/Elsevier, (2009)

[14] M. Villiger, C. Pache, and T. Lasser, "Dark-field optical coherence microscopy," *Opt. Lett.* 35, 3489-3491 (2010)

[15] A. Yariv, Optical Electronics in Modern Communications (Oxford University, New York, 1991).

[16] X. Chen, K. L. Reichenbach, and C. Xu, "Experimental and theoretical analysis of core-to-core coupling on fiber bundle imaging," Opt. Express 16, 21598-21607 (2008).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A dark field endoscopic microscope, comprising:
    an illumination system;
    an objective lens unit arranged in an optical path of said illumination system;
    an optical fiber bundle comprising optical fibers optically coupled to said objective lens unit, said optical fiber bundle extending along a length direction; and
    an observation system comprising a two-dimensional imaging sensor arranged in an optical return path from said optical fibers of said optical fiber bundle,
    wherein said illumination system provides oblique off-axial illumination of a field of view of said dark field endoscopic microscope while axial rays are at least attenuated,
    wherein said observation system forms, using said two-dimensional imaging sensor, a two-dimensional image of an object within said field of view while being illuminated by said oblique off-axial illumination,
    wherein said Objective lens is arranged between said illumination system and said optical fiber bundle,
    wherein said objective lens focuses light from said illumination system onto said optical fiber bundle such that said light enters said optical fiber bundle at an angle that is oblique to said length direction of said fiber bundle,
    wherein said objective lens is positioned to simultaneously illuminate all fibers of said optical fiber bundle with said light, and
    wherein said observation system blocks light exiting said fiber bundle at said angle that is oblique to said length direction of said fiber bundle while transmitting light that is parallel to said length direction of said fiber bundle.

2. The dark field endoscopic microscope according to claim 1, wherein said illumination system comprises:
    a light source,
    a collimating lens system, and
    an opaque disk arranged to block axial rays from said light source.

3. The dark field endoscopic microscope according to claim 2, wherein said light source is a white light source.

4. The dark field endoscopic microscope according to claim 3, wherein said light source is a light emitting diode white light source.

5. The dark field endoscopic microscope according to claim 3, wherein said light source is a narrowband light emitting diode light source.

6. The dark field endoscopic microscope according to claim 1, wherein said observation system comprises an aperture stop arranged to block specular reflection of illumination light from a proximal end of said optical fiber bundle while allowing light returned from a specimen under observation to pass therethrough.

7. The dark field endoscopic microscope according to claim 6, wherein said observation system further comprises an imaging detector arranged after said aperture stop to provide imaging signals for digital imaging.

8. The dark field endoscopic microscope according to claim 7, wherein said imaging detector provides an image of an entirety of said field of view.

9. The dark field endoscopic microscope according to claim 1, wherein said aperture stop is an adjustable iris.

10. The dark field endoscopic microscope according to claim 1, wherein said optical fiber bundle is replaceable such that a used optical fiber bundle can be replaced by a sterile optical fiber bundle for surgical use.

11. The dark field endoscopic microscope according to claim 1, wherein said illumination system is constructed and arranged to illuminate a plurality of fibers of said optical fiber bundle so as to provide said oblique off-axial illumination simultaneously to an entirety of said field, of view.

12. The dark field endoscopic microscope according to claim 1, wherein said illumination system provides an annular illumination intensity pattern across said optical fiber bundle.

* * * * *